(12) United States Patent
Takaku et al.

(10) Patent No.: US 7,033,828 B2
(45) Date of Patent: Apr. 25, 2006

(54) NUCLEIC ACID ENCODING GAMMA RETINOIC ACID RECEPTOR FUSION PROTEIN

(75) Inventors: Fumimaro Takaku, Tokyo (JP); Takashi Ishikawa, Tokyo (JP); Michio Imawari, Tochigo Pref. (JP); Ronald Mark Evans, La Jolla, CA (US); Kazuhiko Umesono, Kyoto (JP)

(73) Assignees: The Salk Institute for Biological Studies, La Jolla, CA (US); Sloan-Kettering Institute for Cancer Research, New York, NY (US)

( * ) Notice: Subject to any disclaimer, the term of this patent is extended or adjusted under 35 U.S.C. 154(b) by 27 days.

(21) Appl. No.: 09/797,727

(22) Filed: Mar. 1, 2001

(65) Prior Publication Data

US 2004/0171800 A9    Sep. 2, 2004

Related U.S. Application Data

(60) Division of application No. 08/486,325, filed on Jun. 7, 1995, now Pat. No. 6,284,870, which is a continuation of application No. 08/100,039, filed on Jul. 30, 1993, now Pat. No. 5,530,094, which is a division of application No. 07/370,407, filed on Jun. 22, 1989, now Pat. No. 5,260,432.

(51) Int. Cl.
*C12N 15/62*    (2006.01)
*C12N 5/10*    (2006.01)

(52) U.S. Cl. .................................... 435/325; 536/23.4
(58) Field of Classification Search ................ 435/325; 536/23.4
See application file for complete search history.

(56) References Cited

U.S. PATENT DOCUMENTS 5,171,671 A * 12/1992 Evans et al.

* cited by examiner

Primary Examiner—Michael Pak
(74) Attorney, Agent, or Firm—Foley & LardnerLLP; Stephen E. Reiter

(57) ABSTRACT

A novel gamma retinoic acid receptor is disclosed. The novel receptor is encoded for by cDNA carried on plasmid pGEM-hRARγ, which has been deposited with the American Type Culture Collection for patent purposes. Chimeric receptor proteins are also disclosed. The chimera contain at least one functional domain from the new gamma retinoic acid receptor.

6 Claims, 4 Drawing Sheets

FIG. 1A

```
1   GAATTCGGCTCAACCTGACCCAGTATGTAGAAGCCAGTCTC
43  TGCAGGCGGGCCAGCGGGGACTTTTGGAGGCCCAGTGGGCAGGCCCAGGGCCAGGAGCCTCCCAGGCTGGGGCA
121 GTGGGCATGGGCAGGGCAGGGGCTGTGCTGGCTGAAGACCTCGCCCACTGCAGAGGGACTCTCACACCGCAGCTGCC

200  ATG GCC ACC AAT AAG GAG CGA CTC TTT GCG GCT GGT GCC CTG GGG CCT GGA TCT GGC TAC
1    Met Ala Thr Asn Lys Glu Arg Leu Phe Ala Ala Gly Ala Leu Gly Pro Gly Ser Gly Tyr

260  CCA GGG GCA GGT TTC CCC TTC GCC TTC CCA GGG GCA CTC AGG GGG TCT CCG CCT TTC GAG
21   Pro Gly Ala Gly Phe Pro Phe Ala Phe Pro Gly Ala Leu Arg Gly Ser Pro Pro Phe Glu

320  ATG CTG AGC CCT AGC TTC CGG GGC CTG GGC CAG CCT GAC CTC CCC AAG GAG ATG GCC TCT
41   Met Leu Ser Pro Ser Phe Arg Gly Leu Gly Gln Pro Asp Leu Pro Lys Glu Met Ala Ser

380  CTG TCG GAG ACA CAG AGC TCA GAG ATG GTG CCC AGC TCG CCC
61   Leu Ser Val Glu Thr Gln Ser Ser Glu Met Val Pro Ser Pro

440  CCT CCG GTC TAC CGG AAG CCA GTG TGT AAT GAC AAG TCC TCT GGC TAC
81   Pro Pro Val Tyr Arg Lys Pro Val Cys Asn Asp Lys Ser Ser Gly Tyr

500  CAC TAT GGG GTC AGC TCT TGT GAA GGC TGG AAA GGC TGC CGA AGC ATC CAG AAG
101  His Tyr Gly Val Ser Ser Cys Glu Gly Trp Lys Gly Cys Arg Ser Ile Gln Lys

560  AAC ATG GTG TAC ACG TGT CAC CGC GAC CGC AAG TGC TTC GAA GTG ATC ATC AAC AAG GTG ACC AGG AAT
121  Asn Met Val Tyr Thr Cys His Arg Asp Arg Lys Cys Phe Glu Val Ile Ile Asn Lys Val Thr Arg Asn

620  CGC TGC CAG TAC CAG CGG CTA CAG AAG AAG AAA TGC TTC GAA GTG GGC ATG TCC AAG GAA GCT GTG
141  Arg Cys Gln Tyr Gln Arg Leu Gln Lys Lys Lys Cys Phe Glu Val Gly Met Ser Lys Glu Ala Val

680  CGA AAT GAC CGG AAC AAG AAG AAG AAG GTG GAA GAA GGG TCA CCT GAC AGC TAT
161  Arg Asn Asp Arg Asn Lys Lys Lys Lys Val Glu Glu Gly Ser Pro Asp Ser Tyr

740  GAG CTG AGC CCT AGC TTA GAG GAG CTC ATC ACC AAG GTC AGC AAA GCC CAT CAG GAG ACT
181  Glu Leu Ser Pro Ser Leu Glu Glu Leu Ile Thr Lys Val Ser Lys Ala His Gln Glu Thr
```

```
 800 TTC CTC TGC CAG CTG GGC AAG TAT ACC AAC TCC AGT GCA GAC CAC CGC GTG
 201 Phe Pro Ser Leu Cys Gln Leu Gly Lys Tyr Thr Asn Ser Ala Asp His Arg Val
 860 CAG GAT CTG GGG CTG TGG GAC AAG TTC GAG AGT GCT ACC AAG ATC ATC AAG
 221 Gln Asp Leu Gly Leu Trp Asp Lys Phe Ser Glu Ala Thr Lys Ile Ile Lys
 920 ATC GTG GAG TTT GCC AAA CGG TTG CCT GGC TTT ACA ATT GCT GAC CAG ATC
 241 Ile Val Glu Phe Ala Lys Arg Leu Pro Gly Phe Thr Ile Ala Asp Gln Ile
 980 ACT CTG CTC AAA GCT GCC TGC CTA GAT ATC CTG ATG ATC CGT TGC ATC ACC
 261 Thr Leu Leu Lys Ala Ala Cys Leu Asp Ile Leu Met Leu Arg Ile Cys Thr
1040 CCA GAG CAG ATG ACC ATG TCC TTC TCC AAC GGG CTG ACC CTG AAC CGG CAG ATG CAC
1281 Pro Glu Gln Met Thr Met Ser Phe Ser Asn Gly Leu Thr Leu Asn Arg Gln Met His
1100 AAT GCC GAC GGG CCC ACC CTC GAC ACA GAC CTT GTC TTT GCC TTT GCA ATG CTG CCC
1301 Asn Ala Asp Gly Pro Thr Leu Asp Thr Asp Leu Val Phe Ala Phe Ala Met Leu Pro
1160 CTG GAT ATG GAT GAC CTG GAG GGG CTG CTC AGC GAC ATC TGC TGC GGA GAC
1321 Leu Asp Met Asp Asp Leu Glu Gly Leu Leu Ser Asp Ile Cys Cys Gly Asp
1220 CGC ATG TAC TAC CTG GAG GAG GAG CCC CCC AAA GTG CAG CCC CAG GAA GCC
1341 Arg Met Tyr Tyr Leu Glu Glu Glu Pro Pro Lys Val Gln Pro Gln Glu Ala
1280 CTG AGG CTG CTG CTC CGG CGG CGG CGG CCC ATC TTA CCC TAC ATG GCT GAA ATG CTA
1361 Leu Arg Leu Leu Leu Arg Arg Arg Arg Pro Ile Leu Pro Tyr Met Ala Glu Met Leu
1340 ATG AAA ATC ACC GAC CTC CTG CCC CCG ATG CCG TTA CCC ATC ATC GCC ATT ACT CTG
1381 Met Lys Ile Thr Asp Leu Leu Pro Pro Met Pro Leu Pro Ile Ile Ala Ile Thr Leu
1400 AAG ATG GAG GCT ATT GCT CCA CCA GGC ATG CGG GAG GAT GAG ATG ATG CTG GAA
1401 Lys Met Glu Ala Ile Ala Pro Pro Gly Met Arg Glu Asp Glu Met Met Leu Glu
1460 ATG TTT GAG GAT GAC GAC GAT GAC CTC AAC TCG CAG CCT CCC CCA CAC CCC AAT GCC TCT AGC GAG GAT GAG
1421 Met Phe Glu Asp Asp Asp Asp Leu Asn Ser Gln Pro Pro His Pro Asn Ala Ser Ser Glu Asp Glu
1520 GTT CCT GGC CAG GGC GGG AAA GGC CTG GGC CTG AAG TCC CCA GGC TGA GCC CCA GGC CGA ATT (SEQ ID NO:1)
1441 Val Pro Gly Gln Gly Gly Lys Gly Leu Gly Leu Lys Ser Pro Ala End       (SEQ ID NO:2)

FIG. 1B
```

HUMAN RETINOIC ACID RECEPTORS

[amino terminal] A/B REGION FIG. 2

```
γ       MATNKERLFAAGALGPGSGYPGAGFPFAFPGALRGSPPFEMLSPSFRGLGQPDLPKEMAS
α       MASNSSSCPTPG.GHLNGYPVPPYAF FPPML GLSPPGALTTLQHQLPVSGYSTPSP
β              MFDCMDVL.VS..QILD.YTASPSSCMLQEKA.KAC.S...T.TEWQHRHTA

γ       LSVETQSTSSEEMVPSSPSPPPPPRVYKP  89
α       ATI....S....I...P.....L..I...  87
β       Q.I..........L...P...L........  80
```

[DNA binding] C REGION

```
γ  90  CFVCNDKSSGYHYGVSSCEGCKGFFRRSIQKNMVYTCHRDKNCIINKVTRNRCQYCRLQK
α  88  ....Q.........A.............................................
β  81  ....Q.........A..................I..........V...............

γ      CFEVGM  155
α      ......  153  (97%)
β      ......  146  (94%)
```

[hinge] D REGION

```
γ 156  SKEAVRNDRNKKKKEVKEEGSPDSYELSPQLEELITKVSKAHQETF  201
α 154  ...S...........PKPECSE..T.T.EVG...E..R.......  199
β 147  ...S...........TSKQECTE...MTAE.DD.TE.IR.......  192
```

[ligand binding] E REGION

```
γ 202  PSLCQLGKYTTNSSADHRVQLDLGLWDKFSELATKCIIKIVEFAKRLPGFTGLSIADQIT
α 200  .A..........N.SEQ..S..ID.:......S......T.....Q.....T.T......
β 193  ..............R..............................T......

γ      LLKAACLDILMLRICTRYTPEQDTMTFSDGLTLNRTQMHNAGFGPLTDLVFAFAGQLLPL
α      .............I.................................N.....
β      .............I.................................T..N.....

γ      EMDDTETGLLSAICLICGDRMDLEEPEKVDKLQEPLLEALRLYARRRRPSQPYMFPRMLM
α      ....A...............Q...Q.DR..M.........KV.V.K....R.H...K...
β      ....................Q.....T.............KI.I.K....K.H...KI..

γ      KITDLRGISTKGAESAITLKMEIPGPMPPLIREMLENPEM  421
α      ......S..A.....V.........S.....Q.....S.G  419  (84%)
β      ......S..A.....V.........S.....Q..M..S.G  412  (90%)
```

[carboxyl terminal] F REGION

```
γ 422  FEDDSSQPGPHPNASSEDEVPGGQGKGGLKSPA*                  454    (SEQ ID NO:2)
α 420  LDTL.G...GGGRDGGGLAP.P.SCSPS.SPSSNRSSPATHSP*        462    (SEQ ID NO:3)
β 413  H.PLTPSSSGNTAEH.PSIS.SSVENS.VSQSPLVQ*              448    (SEQ ID NO:4)
```

γ = GAMMA RETINOIC ACID RECEPTOR
α = ALPHA RETINOIC ACID RECEPTOR
β = BETA RETINOIC ACID RECEPTOR

NUCLEIC ACID ENCODING GAMMA RETINOIC ACID RECEPTOR FUSION PROTEIN

FIELD OF THE INVENTION

The present invention relates generally to ligand-responsive regulatory proteins and genes encoding them. More particularly, the present invention relates to a new retinoic acid receptor protein and the gene that encodes it, modification of the new retinoic acid receptor protein and gene by recombinant DNA and other genetic engineering techniques, plus uses of the new retinoic acid receptor protein and gene, both unmodified and modified.

BACKGROUND OF THE INVENTION

It is known that hormones like the glucocorticoid and thyroid hormones enter cells by facilitated diffusion. It is also known that hormones then bind to specific receptor proteins, thereby creating a hormone/receptor complex. The binding of hormone to the receptor initiates an alosteric alteration of the receptor protein. As a result of this alteration, it is believed that the hormone/receptor complex is capable of binding with high affinity to certain specific sites on the chromatin DNA. Such sites, which are referred to as hormone response elements or HRE's, modulate expression of nearby target gene promoters.

A major obstacle to further understanding of the specifics of gene regulation by exogenous inducers such as hormones has been the lack of availability of receptor proteins in sufficient quantity and purity to allow such proteins to be adequately analyzed and characterized. This same lack of availability has thwarted the use of receptors in diagnostic assays to determine the presence of exogenous inducers (e.g., the hormones) in various body fluids and tissues, as well as their use as "prototypes" for engineering chimeric receptor protein analogs.

In an effort to overcome this lack of availability of receptor proteins, scientific investigators are working to discover the genes that encode such proteins. To date several such genes have been disclosed and characterized. The cloned genes include those encoding the following receptors: glucocorticoid, mineralocorticoid, progesterone, estrogen, the two steroid-related receptors (known in the art as ERR1 and ERR2), vitamin $D_3$, thyroid, v-erb-A, E75 (*Drosophilia* and two retinoid receptor proteins, retinoic acid receptor alpha (RARα) and retinoic acid receptor beta (RARβ). (See Giguere, et al. (1987) regarding RARα, and Petkovich, et al. (1987) and Brand, et al. (1988) regarding RARβ.).

This disclosure describes the isolation and characterization of a cDNA encoding a third functional retinoid receptor protein that is referred to herein as the gamma retinoic acid receptor (RARγ). Like RARs alpha and beta, the new gamma retinoic acid receptor has homology with the DNA-binding and ligand-binding domains of the steroid and thyroid hormone receptors.

The retinoic acid receptor genes belong to the superfamily of genes known as the steroid hormone receptor family. All genes in this family can be divided into discrete regions or domains that are sometimes referred to as regions A/B, C, D, E, and F. See FIG. 2 (SEQ ID NOS:2–4); also see Robertson, (1987) and Evans, (1988). The C region encodes the DNA-binding domain, the E region encodes the ligand-binding domain and the F region encodes the carboxy-terminus domain. The D region is believed to function as a "hinge". The function of the A/B (or N-terminus) region is not entirely clear; it may be involved with enhancement and repression of receptor transcription activity. See for example, Hollenberg, et al., (1988) and Oro, et al., (1988).

The present specification also discloses chimeric receptors made by "swapping" functional domains between the new gamma retinoic acid receptor and the glucocorticoid, the mineralocorticoid, the progesterone, the estrogen, the estrogen-related (ERR1 and ERR2), the vitamin $D_3$ receptor, the thyroid receptors, the V-erb-A receptor, the E75 (*Drosophilia*) receptor and the alpha and beta retinoic acid receptors. These chimeric receptors have hybrid functional characteristics based on the "origin" of the "parental" DNA-binding and ligand-binding domains incorporated within the chimeras. For example, if the DNA-binding domain in the chimeric receptor is the gamma retinoic acid receptor DNA-binding domain (i.e., is obtained from wild-type gamma retinoic acid receptor or is a mutant that contains the functional elements of the gamma retinoic acid DNA-binding domain), then the chimera will have DNA-binding properties characteristic of the gamma retinoic acid receptor. The same is true of the ligand-binding domain.

DESCRIPTION OF THE DRAWINGS

The drawings comprise three figures of which:

FIG. 1 is a drawing which shows the DNA nucleotide sequence (SEQ ID NO:1) and the primary protein sequence (SEQ ID NO:2) of hRARγ encoded by the EcoRI fragment harbored in pGEM-hRARγ.

FIG. 2 is a drawing that shows the amino acid comparison among the three human RARs (alpha, beta and gamma) (SEQ ID NOS:2–4).

FIG. 3 (A and B) is composed of two blots.

DEFINITIONS

Figure 3A:
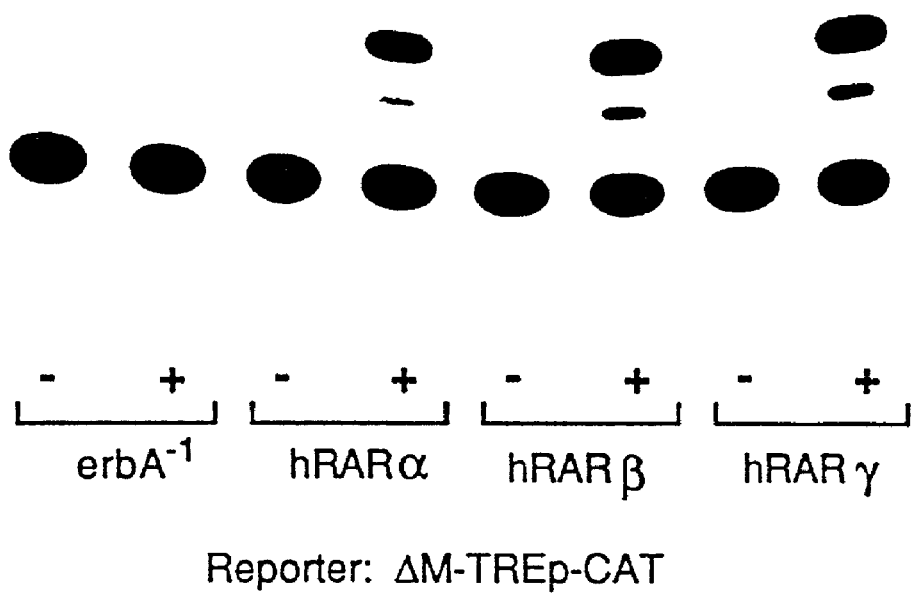
FIG. 3A shows induction of CAT activity and thus retinoic acid-dependent transactivation by the protein encoded by the cDNA insert of pGEM-hRARγ.

In the present specification and claims, reference will be made to phrases and terms of art which are expressly defined for use herein as follows:

As used herein, the generic term "retinoids" means a group of compounds which includes retinoic acid, vitamin A (retinol) and a series of natural and synthetic derivatives that can exert profound effects on development and differentiation in a wide variety of systems.

As used herein, the human species is identified with a lower case "h".

As used herein, "steroid hormone superfamily of receptors" refers to the class of related receptors comprised of glucocorticoid, mineralocorticoid, progesterone, estrogen, estrogen-related (ERR1 and ERR2), vitamin $D_3$, thyroid, v-erb-A, E75 (*Drosophilia*) and the retinoic acid receptors. See Evans (1988) and the references cited therein.

As used herein, RAR means retinoic acid receptor. The acronym hRAR means human retinoic acid receptor. hRARα refers to human retinoic acid receptor alpha. See Giguere, et al., (1987). hRARβ refers to human retinoic acid receptor beta. See Brand, et al., (1988). hRARγ refers to human retinoic acid receptor gamma.

As used herein, GR means glucocorticoid receptor. hGR means human glucocorticoid receptor.

As used herein, MR means mineralocorticoid receptor. hMR means human mineralocorticoid receptor.

As used herein, $T_3R$ means thyroid hormone receptor triiodthyronine. $T_3R\alpha$ and $T_3R\beta$ refer to the alpha and beta forms of the thyroid receptor.

As used herein, ER means estrogen receptor.

As used herein, ERR means estrogen-related receptor. The acronyms, hERR1 and hERR2 refer to human estrogen-related receptors 1 and 2. These receptors are more related to steroid receptors than to the thyroid receptors, yet they do not bind any of the major classes of known steroid hormones (Giguere, et al., 1988).

As used herein, VDR means vitamin $D_3$ receptor.

As used herein, PR means progesterone receptor.

As used herein, CAT means chloramphenicol acetyltransferase.

As used herein, CV-1 means mouse kidney cells from the cell line referred to as "CV-1". CV-1 cells are receptor-deficient cells that are useful in functional ligand identification assays.

As used herein, hormone response elements or HRE's mean short cis-acting DNA sequences (about 20 bp in size) that are required for hormonal (or ligand) activation of transcription. The attachment of these elements to an otherwise hormone-nonresponsive gene causes that gene to become hormone responsive. These sequences function in a position- and orientation-independent fashion. Unlike other transcriptional regulators, the activity of the HRE's is dependent upon the presence or absence of ligand. See Evans (1988) and the references cited therein.

As used herein, synthetic HRE's refer to HRE's that have been synthesized in vitro using automated nucleotide synthesis machines. Since the HRE's are only about 20 bp in size, they are easily synthesized in this manner. If wild-type, engineered or synthetic HREs are linked to hormone-nonresponsive promoters, these promoters become hormone responsive. See Evans (1988) and the references cited therein.

As used herein, the acronym GRE means glucocorticoid response element and TRE means thyroid receptor response element. ($TRE_p$ is a TRE that has been engineered to maximize the palindrominicity of this response element.) GRE's are hormone response elements that confer glucocorticoid responsiveness via interaction with the GR. See Payvar, et al., *Cell* 35:381 (1983) and Schiedereit, et al., *Nature* 304:749 (1983). GRE's can be used with any wild-type or chimeric receptor whose DNA-binding domain can functionally bind (i.e., activate) with the GRE. For example, since GR, MR and PR receptors can all activate GRE's, a GRE can be used with any wild-type or chimeric receptor that has a GR, MR or PR-type DNA-binding domain. TRE's are similar to GRE's except that they confer thyroid hormone responsiveness via interaction with TR. TRE's can be used with any wild-type or chimeric receptor whose DNA-binding domain can functionally bind (i.e., activate) with the TRE. Both thyroid and retinoic acid receptors can activate TRE's, so a TRE can be used with any receptor that has a TR or RAR-type DNA-binding domain.

As used herein, ligand means an inducer, such as a hormone or growth substance. Inside a cell, the ligand binds to a receptor protein, thereby creating a ligand/receptor complex, which in turn can bind to an appropriate hormone response element. Single ligands may have multiple receptors. For example, both the $T_3R_\alpha$ and the $T_3R_\beta$ bind thyroid hormone such as $T_3$.

As used herein, the phrase "DNA-binding domain" refers to that portion of the receptor protein (such as glucocorticoid, mineralocorticoid, progesterone, estrogen, estrogen-related receptors, vitamin $D_3$, thyroid, v-erb-A, E75 (*Drosophilia*) and the retinoic acid receptors) that binds to HRE sites on the chromatin DNA. The boundaries for these DNA-binding domains have been identified and characterized for the steroid hormone superfamily. See Evans (1988) and the references cited therein.

The DNA-binding domains of the steroid hormone superfamily of receptors consist of an amino segment varying between 66 to 68 amino acids in length. This segment contains 9 cysteine residues, one of which is the first amino acid of the segment. This first Cys residue begins a motif described as Cys-$X_2$-Cys-$X_{13-15}$-Cys-$X_2$-Cys, (SEQ ID NOS:5–7) where X is any amino acid residue. The DNA-binding domain invariably ends with the amino acids Gly-Met.

For convenience in the cloning procedure, between 1 and 6 amino acids residues preceding and/or following the DNA-binding domain can be switched along with the DNA-binding domain.

As used herein, the phrase "ligand-binding domain region" refers to that portion of the receptor proteins that binds to ligands such as growth substances or hormones. These boundaries of the ligand-binding domains for the steroid receptor superfamily have been identified and characterized. See Evans (1988) and the references cited therein.

Common restriction endonuclease sites must be introduced into receptor cDNA clones to allow exchange of functional domains between receptors. In any of the various receptors in the steroid receptor superfamily of genes, the first common site can be introduced immediately preceding the DNA-binding domain, the second common site immediately following it. (For example, in any of the steroid hormone superfamily, a unique NotI site can be introduced immediately preceding the region of the cDNA encoding the DNA-binding domain and a unique XhoI site can be introduced immediately following it. This divides the receptors into three functional regions or "cassettes"; (1) an N-terminus cassette, (2) a DNA-binding domain cassette, and (3) a ligand-binding domain cassette. The three regions or cassettes from any one receptor can be combined with cassettes from other receptors to create a variety of chimeric receptors.

As used herein, "mutant" DNA refers to DNA which has been genetically engineered to be different from the "wild-type" or unmodified sequence. Such genetic engineering can include the insertion of nucleotides into wild-type sequences, deletion of nucleotides from wild-type sequences, substitution of nucleotides in the wild-type sequences, or "swapping" of functional domains from one receptor to another. Receptors that have been engineered by "swapping" functional domains from one receptor to another are also referred to as chimeric or hybrid receptors. Chimeric receptors can be further engineered by insertion of nucleotides, deletion of nucleotides, substitution of nucleotides, etc.

Use of the term "substantial sequence homology" in the present specification and claims refers to DNA, RNA, or amino acid sequences that have slight and non-consequential sequence variations from the actual sequences disclosed and claimed herein and means that these sequences are within the scope of the appended claims. In this regard, the "slight and non-consequential" sequence variations mean that the homologous sequences will function in substantially the same manner to produce substantially the same compositions as the nucleic acid and amino acid compositions disclosed and claimed herein.

As used herein, the term "recombinantly produced" means made using genetic engineering techniques, not merely purified from nature.

The amino acids which comprise the various amino acid sequences appearing herein may be identified according to the following three-letter or one-letter abbreviations:

| Amino Acid | Three-Letter Abbreviation | One-Letter Abbreviation |
|---|---|---|
| L - Alanine | Ala | A |
| L - Arginine | Arg | R |
| L - Asparagine | Asn | N |
| L - Aspartic Acid | Asp | D |
| L - Cysteine | Cys | C |
| L - Glutamine | Gln | Q |
| L - Glutamic Acid | Glu | E |
| L - Histidine | His | H |
| L - Isoleucine | Ile | I |
| L - Leucine | Leu | L |
| L - Lysine | Lys | K |
| L - Methionine | Met | M |
| L - Phenylalanine | Phe | F |
| L - Proline | Pro | P |
| L - Serine | Ser | S |
| L - Threonine | Thr | T |
| L - Tryptophan | Trp | W |
| L - Tyrosine | Tyr | Y |
| L - Valine | Val | V |

The nucleotides which comprise the various nucleotide sequences appearing herein have their usual single-letter designations (A, G, T, C or U) used routinely in the art.

As used herein, bp means base pairs and kb means kilobase pairs.

DEPOSITS

Plasmid pGEM-hRARγ was deposited Jun. 22, 1989 at the American Type Culture Collection, Manassas, Va., U.S.A. (ATCC) for patent purposes. It has been accorded ATCC No. 40623.

DESCRIPTION OF THE INVENTION

In one aspect, the present invention comprises a double-stranded DNA segment wherein the plus or sense strand encodes the primary sequence of a protein that has ligand-binding and DNA-binding properties characteristic of a retinoid receptor protein referred to herein as human gamma retinoic acid receptor protein. According to this aspect of the invention, the double-stranded DNA segment is one which is capable of being expressed into human gamma retinoic acid receptor protein.

In another aspect, the invention comprises a single-stranded DNA, which is the sense strand of a double-stranded DNA coding for retinoic acid receptor gamma protein.

In another aspect, the invention comprises an mRNA made by transcription of the double-stranded DNA of the invention.

In another aspect, the invention comprises a plasmid, pGEM-hRARγ, which contains DNA encoding the human gamma retinoic acid receptor protein of the present invention (hRARγ). This plasmid has been deposited with the American Type Culture Collection for patent purposes; it has been accorded ATCC No. 40623.

In still another aspect, the invention comprises a cell, preferably a mammalian cell, transfected with a DNA coding for retinoic acid receptor gamma protein. According to this aspect of the invention, the transfected DNA is capable of being expressed in the cell, thereby increasing the amount of gamma retinoic acid receptor encoded by this DNA in the cell.

Further the invention comprises novel retinoic acid receptors made by expression of DNA coding for gamma retinoic acid receptor or translation of an mRNA transcribed from such gamma retinoic acid receptor encoding DNA. According to this aspect of the invention, the gamma retinoic acid receptors will be protein products of "unmodified" gamma retinoic acid encoding DNA's and mRNA's, or will be modified or genetically engineered gamma retinoic acid receptor protein products which, as a result of engineered mutations in the receptor DNA sequences, will have one or more differences in amino acid sequence from the corresponding naturally occurring "wild-type" gamma retinoic acid receptor proteins. Preferably these gamma retinoic acid receptors, whether "unmodified" or "engineered", will have at least about 5% (over background) of the retinoic acid binding activity and/or at least about 5% (over background) of the DNA-binding or transcription-activating activity of the corresponding naturally occurring gamma retinoic acid receptor.

Further the invention comprises chimeric receptors made by exchanging the functional domains of the gamma retinoic acid receptor with functional domains of another type. The chimeric DNA's thus produced encode chimeric receptor proteins that have functional characteristics based on the "origin" of their respective DNA- and ligand-binding domains.

The chimeric receptors of the invention include double-stranded DNA's that encode the chimeric receptors, as well as single-stranded DNA's which are the sense strands of the double-stranded DNA's, and mRNA's made by transcription of the double-stranded DNA's. The invention also comprises cells, both eukaryotic and prokaryotic, that are transfected with chimeric receptors encoding DNA of the invention.

According to the preferred method for making the chimeric receptor genes and proteins of the present invention, to effect the chimeric DNA fusions, two restriction endonuclease sites are preferably introduced into each receptor DNA at comparable locations in or near the DNA-binding domains in order to divide the receptor DNA's into three functional domains or regions. (For example, a unique NotI site can be introduced immediately preceding the DNA-binding domain and a unique XhoI site can be introduced immediately following it. This divides the receptors into three functional regions or "cassettes"; (1) an N-terminus cassette, (2) a DNA-binding domain cassette, and (3) a ligand-binding domain cassette. The three regions or cassettes from the RARγ receptor can be combined with cassettes from other receptors from the steroid superfamily to create a variety of chimeric receptors.

EXPERIMENTAL ASPECTS OF THE INVENTION

Isolation of the Gamma Retinoic Acid Receptor

An oligonucleotide from RARα was labeled and used to probe a human cDNA library constructed from human tumor liver cell mRNA. Nucleotide sequence analysis of one of the clones thus isolated revealed a long open reading frame of 454 amino acids beginning with a presumptive initiator methionine codon at position 200 as shown in FIG. 1 (SEQ ID NOS:1–2).

RAR Amino Acid Sequence Comparison

The amino acid sequence of the newly discovered RARγ (SEQ ID NO:2) was compared with the amino acid sequences from RARα (SEQ ID NO:3) and hRARβ (SEQ ID NO:4). The results of this comparison are shown in FIG. 2 (SEQ ID NOS:2–4). As the drawing in the figure illustrates, remarkable identity in the amino acid sequence exists in the DNA-binding domains and in the ligand-binding domains.

Ligand Assay

To assay for the ligand for the putative new retinoic acid gamma receptor protein, the NcoI-EcoRI fragment of pGEM-hRARγ was recloned in the pRS eukaryotic expression vector giving pRShRARγ. The plasmid was introduced into monkey kidney CV-1 cells via calcium-phosphate transfection together with a reporter plasmid ΔMTV-TRE$_p$-CAT. As a control, pRSerbA$^{-1}$ (encodes no protein, stands as a negative control), pRShRARα, and pRShRARβ were also examined. The transfected cells were incubated in the presence or absence of 100 nM retinoic acid for 36 hours, and the induced CAT activities were analyzed by chromatography. The results indicate that a protein encoded by the NcoI-EcoRI insert transactivates through the ΔMTV-TRE$_p$ promoter in a retinoic acid dependent fashion, providing evidence that it is a functional new retinoic acid receptor. See FIG. 3A.

Response Element Specificity of hRARγ

Figure 3B:
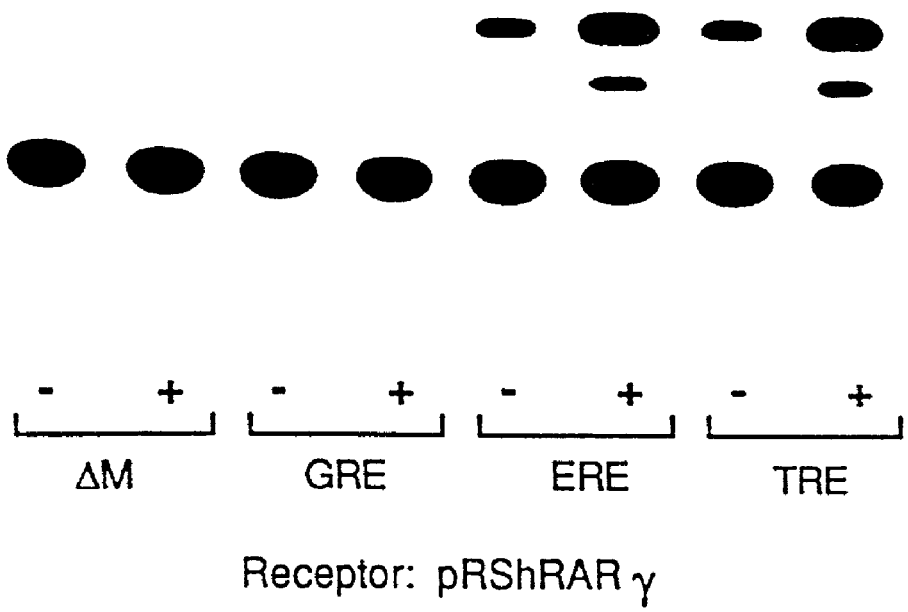
FIG. 3B shows that hRARγ recognizes ERE and TRE, but not GRE.

To assay for the hormone response elements activated by the putative new gamma retinoic acid receptor protein, the NcoI-EcoRI fragment of pGEM-hRARγ was recloned in the pRS eukaryotic expression vector giving pRShRARγ. The plasmid was introduced into monkey kidney CV-1 cells via calcium-phosphate transfection together with one of the following reporter plasmids: ΔMTV-GRE-CAT, ΔMTV-ERE-CAT, or ΔMTV-TRE-CAT, with ΔMTV-CAT as the control. As above, the transfected cells were incubated in the presence or absence of 100 nM retinoic acid for 36 hours, and the induced CAT activities were analyzed by chromatography. As FIG. 3B illustrates, hRARγ recognizes ERE and TRE, but not GRE, which is consistent with the other two known human retinoic acid receptors.

Gamma Retinoic Acid Receptor Data Summary

The data disclosed herein identify the protein product encoded by the cDNA insert in pGEM-hRARγ as human gamma retinoic acid receptor based on three criteria. First, the overall structural homology that the pGEM-hRARγ gene product has with hRARα and hRARβ suggests that it is a retinoic acid receptor. Second, the RARγ receptor protein acts as a transcriptional regulator of a TRE- or an ERE-inducible reporter gene in the presence of retinoic acid. Third, the hRARγ recognizes ERE and TRE, but not GRE.

REFERENCES

The present specification refers to the following publications, each of which is expressly incorporated by reference herein.
1. Brand, N., Petkovich, M., Krust, A., and Chambon, P., "Identification of a Second Human Retinoic Acid Receptor", *Nature* 332, 850–853 (1988).
2. Evans, R., "The Steroid and Thyroid Hormone Receptor Superfamily", *Science* 240, 889–895 (1988).
3. Giguere, V., Ong, E. S., Segui, P., and Evans, R. M., "Identification of a Receptor for the Morphogen Retinoic Acid", *Nature* 330, 624–629 (1987).
4. Giguere, V., Yang, N., Segui, P., and Evans, R. M., *Nature* 331, 91- (1988).
5. Hollenberg, S. and Evans, R. M., "Multiple and Coperative Trans-Activation Domains of the Human Glucocorticoid Receptor", *Cell,* 55, 899–906 (1988).
6. Kozak, M., *Nucleic Acid Res.* 16, 8125–8148 (1987).
7. Oro, A. E., Hollenberg, S., and Evans, R. M., *Cell,* 55, 1109–1114 (1988).
8. Petkovich, M., Brand, N. J., Krust, A., and Chambon, P., "A Human Retinoic Acid Receptor Which Belongs to the Family of Nuclear Receptors", *Nature* 330, 444–450 (1987).
9. Robertson, M., "Towards a Biochemistry of Morphogenesis", *Nature* 330, 420–421 (1987).

SPECIFICATION SUMMARY

From the foregoing description, one of ordinary skill in the art can understand that the present invention provides substantially pure DNA which encodes the retinoid receptor protein referred to as the gamma retinoic acid receptor protein. The invention also provides a plasmid containing the gamma retinoic acid receptor DNA. This plasmid, pGEM-hRARγ has been deposited with the American Type culture Collection for patent purposes.

The invention is also comprised of gamma retinoic acid receptor proteins, including modified functional forms thereof, expressed from the DNA (or mRNA) of the invention.

The present invention also includes chimeric hybrid receptors made by exchanging (1) the N-terminal domains, (2) the DNA-binding domains, and (3) the ligand-binding domains from hGR, hMR, PR, hERR1, hERR2, T$_3$R$_α$, T$_3$R$_β$, D$_3$, V-erb-A, E75 and the alpha and beta RAR receptors with the domains of the new RARγ receptor. The chimeric receptors so constructed have DNA-binding domain and ligand-binding domain characteristics of the DNA-binding domain and ligand-binding domains of the respective "parental" receptors from which they originated.

The hRARγ DNA of the invention can be used to make the gamma retinoic acid receptor proteins, and functional modified forms thereof, in quantities that were not previously possible. The same is true of the chimeric receptors. With the quantities of gamma receptor protein available as a result of the present invention, the receptor proteins can be used to screen for gamma retinoic acid receptor-agonists or gamma retinoic acid receptor-antagonists. Availability of the gamma receptor proteins also means that they can be used in diagnostic assays to determine levels of retinoic acid present in various tissues and body fluids. Alternatively, the receptor proteins can be used to assay for levels of mRNA.

Without departing from the spirit and scope of this invention, one or ordinary skill can make various changes and modifications to the invention to adapt it to various usages and conditions. As such, these changes and modifications are properly, equitable, and intended to be, within the full range of equivalence of the following claims.

What is claimed is:

1. A nucleic acid encoding a chimeric receptor having an N-terminus domain, a DNA-binding domain, and a ligand-binding domain,
wherein the N-terminus domain of said chimeric receptor is obtained from the N-terminus domain of retinoic acid receptor-alpha (RARα), retinoic acid receptor-beta (RARβ), retinoic acid receptor-gamma (RARγ), glucocorticoid receptor (GR), mineralocorticoid receptor (MR), progesterone receptor (PR), estrogen receptor (ER), vitamin D₃ receptor (VDR), thyroid receptor (TR), the v-erb-A receptor, or the *Drosophila* E75 receptor,
wherein the DNA-binding domain of said chimeric receptor is obtained from the DNA-binding domain of RARα, RARβ, RARγ, GR, MR, PR, ER, VDR, TR, the v-erb-A receptor, or the *Drosophila* E75 receptor, and
wherein the ligand-binding domain of said chimeric receptor is obtained from the ligand-binding domain of RARα, RARβ, RARγ, GR, MR, PR, ER, ERR1, ERR2, VDR, TR, the v-erb-A receptor, or the *Drosophila* E75 receptor,
wherein at least one of the domains of said chimeric receptor comprises a contiguous portion unique to RARγ selected from the group consisting of a nucleotide sequence encoding amino acid residues 1–89 of hRARγ set forth in FIG. 1, a nucleotide sequence encoding an amino acid sequence having greater than 97% identity with amino acid residues 90–155 of hRARγ set forth in FIG. 1, and a nucleotide sequence encoding an amino acid sequence having greater than 90% identity with amino acid residues 202–421 of hRARγ set forth in FIG. 1, and
wherein said chimeric receptor has at least 5% of the DNA-binding, the transcription-activating activity, and/or the ligand-binding activity of RAR$_γ$.

2. A host cell containing nucleic acid according to claim 1.

3. A nucleic add encoding a chimeric receptor according to claim 1,
wherein the N-terminus domain of said chimeric receptor is obtained from the N-terminus domain of glucocorticoid receptor (GR),
wherein the DNA-binding domain of said chimeric receptor is obtained from the DNA-binding domain of RARγ, and has an amino acid sequence having greater than 97% identity with amino acid residues 90–155 of hRARγ set forth in FIG. 1, and
wherein the ligand-binding domain of said chimeric receptor is obtained from the ligand-binding domain of GR.

4. A nucleic acid encoding a chimeric receptor having an N-terminus domain, a DNA-binding domain, and a ligand-binding domain,
wherein the N-terminus domain of said chimeric receptor is obtained from the N-terminus domain of retinoic acid receptor-alpha (RARα), retinoic acid receptor-beta (RARβ), retinoic acid receptor-gamma (RARγ), glucocorticoid receptor (GR), mineralocorticoid receptor (MR), progesterone receptor (PR), estrogen receptor (ER), vitamin D₃ receptor (VDR), thyroid receptor (TR), the v-erb-A receptor, or the *Drosophila* E75 receptor,
wherein the DNA-binding domain of said chimeric receptor is obtained from the DNA-binding domain of RARα, RARβ, RARγ, GR, MR, PR, ER, VDR, TR, the v-erb-A receptor, or the *Drosophila* E75 receptor, and
wherein the ligand-binding domain of said chimeric receptor is obtained from the ligand-binding domain of RARα, RARβ, RARγ, GR, MR, PR, ER, VDR, TR, the v-erb-A receptor, or the *Drosophila* E75 receptor,
wherein at least one of the domains of said chimeric receptor comprises a contiguous portion unique to RARγ selected from the group consisting of a nucleotide sequence encoding amino acid residues 1–89 of hRARγ set forth in FIG. 1, a nucleotide sequence encoding amino acid residues 90–155 of hRARγ set forth in FIG. 1, and a nucleotide sequence encoding amino acid residues 202–421 of hRARγ set forth in FIG. 1, and
wherein said chimeric receptor has at least 5% of the DNA-binding, the transcription-activating activity and/or the ligand-binding activity of RARγ.

5. A host cell containing a nucleic acid according to claim 4.

6. A nucleic acid encoding a chimeric receptor according to claim 4,
wherein the N-terminus domain of said chimeric receptor is obtained from the N-terminus domain of glucocorticoid receptor (GR),
wherein the DNA-binding domain of said chimeric receptor is obtained from the DNA-binding domain of RARγ, and has the amino acid sequence of amino acid residues 90–155 of hRARγ set forth in FIG. 1, and
wherein the ligand-binding domain of said chimeric receptor is obtained from the ligand-binding domain of GR.

* * * * *

UNITED STATES PATENT AND TRADEMARK OFFICE
CERTIFICATE OF CORRECTION

| | | |
|---|---|---|
| PATENT NO. | : 7,033,828 B2 | Page 1 of 1 |
| APPLICATION NO. | : 09/797727 | |
| DATED | : March 1, 2001 | |
| INVENTOR(S) | : Fumimaro Takaku et al. | |

It is certified that error appears in the above-identified patent and that said Letters Patent is hereby corrected as shown below:

Claim 1, column 21, line 29: delete "ERR1, ERR2,"

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,033,828 B2  Page 1 of 1
APPLICATION NO. : 09/797727
DATED : April 25, 2006
INVENTOR(S) : Fumimaro Takaku et al.

It is certified that error appears in the above-identified patent and that said Letters Patent is hereby corrected as shown below:

Claim 1, column 21, line 29: delete "ERR1, ERR2,"

This certificate supersedes Certificate of Correction issued November 7, 2006.

Signed and Sealed this

Twelfth Day of December, 2006

JON W. DUDAS
*Director of the United States Patent and Trademark Office*

SEQUENCE LISTING

<160> NUMBER OF SEQ ID NOS: 7

<210> SEQ ID NO 1

```
<211> LENGTH: 1577
<212> TYPE: DNA
<213> ORGANISM: Human
<220> FEATURE:
<221> NAME/KEY: misc_feature
<223> OTHER INFORMATION: Human Retinoic Acid Receptor-gamma (hRAR-gamma)
<221> NAME/KEY: CDS
<222> LOCATION: (200)..(1576)

<400> SEQUENCE: 1
```

| | | |
|---|---|---|
| gaattcggct caacctgacc cagtatgtag aagccagtct ctgcaggcgg ccagcgggac | | 60 |
| ttttggaggc ccagtgggca ggccaggcag ggcgggtacg gagcctccca ggctggggca | | 120 |
| gtgggcatgg gcagggctg tggctgaaga cctcgcccgc ccactgcaga ccccagggga | | 180 |
| ctctcacacc gcagctgcc atg gcc acc aat aag gag cga ctc ttt gcg gct | | 232 |
|   Met Ala Thr Asn Lys Glu Arg Leu Phe Ala Ala | | |
|   1               5                  10 | | |
| ggt gcc ctg ggg cct gga tct ggc tac cca ggg gca ggt ttc ccc ttc | | 280 |
| Gly Ala Leu Gly Pro Gly Ser Gly Tyr Pro Gly Ala Gly Phe Pro Phe | | |
|         15                  20                  25 | | |
| gcc ttc cca ggg gca ctc agg ggg tct ccg cct ttc gag atg ctg agc | | 328 |
| Ala Phe Pro Gly Ala Leu Arg Gly Ser Pro Pro Phe Glu Met Leu Ser | | |
|     30                  35                  40 | | |
| cct agc ttc cgg ggc ctg ggc cag cct gac ctc ccc aag gag atg gcc | | 376 |
| Pro Ser Phe Arg Gly Leu Gly Gln Pro Asp Leu Pro Lys Glu Met Ala | | |
|  45                  50                  55 | | |
| tct ctg tcg gtg gag aca cag agc acc agc tca gag gag atg gtg ccc | | 424 |
| Ser Leu Ser Val Glu Thr Gln Ser Thr Ser Ser Glu Glu Met Val Pro | | |
| 60                  65                  70                  75 | | |
| agc tcg ccc tcg ccc cct ccg cct cct cgg gtc tac aag cca tgc ttc | | 472 |
| Ser Ser Pro Ser Pro Pro Pro Pro Arg Val Tyr Lys Pro Cys Phe | | |
|                 80                  85                  90 | | |
| gtg tgc aat gac aag tcc tct ggc tac cac tat ggg gtc agc tct tgt | | 520 |
| Val Cys Asn Asp Lys Ser Ser Gly Tyr His Tyr Gly Val Ser Ser Cys | | |
|             95                 100                 105 | | |
| gaa ggc tgc aag ggc ttc ttt cgc cga agc atc cag aag aac atg gtg | | 568 |
| Glu Gly Cys Lys Gly Phe Phe Arg Arg Ser Ile Gln Lys Asn Met Val | | |
|         110                 115                 120 | | |
| tac acg tgt cac cgc gac aaa aac tgt atc atc aac aag gtg acc agg | | 616 |
| Tyr Thr Cys His Arg Asp Lys Asn Cys Ile Ile Asn Lys Val Thr Arg | | |
|     125                 130                 135 | | |
| aat cgc tgc cag tac tgc cgg cta cag aag tgc ttc gaa gtg ggc atg | | 664 |
| Asn Arg Cys Gln Tyr Cys Arg Leu Gln Lys Cys Phe Glu Val Gly Met | | |
| 140                 145                 150                 155 | | |
| tcc aag gaa gct gtg cga aat gac cgg aac aag aag aaa gag gtg | | 712 |
| Ser Lys Glu Ala Val Arg Asn Asp Arg Asn Lys Lys Lys Glu Val | | |
|                 160                 165                 170 | | |
| aag gaa gaa ggg tca cct gac agc tat gag ctg agc cct cag tta gaa | | 760 |
| Lys Glu Glu Gly Ser Pro Asp Ser Tyr Glu Leu Ser Pro Gln Leu Glu | | |
|             175                 180                 185 | | |
| gag ctc atc acc aag gtc agc aaa gcc cat cag gag act ttc ccc tcg | | 808 |
| Glu Leu Ile Thr Lys Val Ser Lys Ala His Gln Glu Thr Phe Pro Ser | | |
|         190                 195                 200 | | |
| ctc tgc cag ctg ggc aag tat acc acg aac tcc agt gca gac cac cgc | | 856 |
| Leu Cys Gln Leu Gly Lys Tyr Thr Thr Asn Ser Ser Ala Asp His Arg | | |
|     205                 210                 215 | | |
| gtg cag ctg gat ctg ggg ctg tgg gac aag ttc agt gag ctg gct acc | | 904 |
| Val Gln Leu Asp Leu Gly Leu Trp Asp Lys Phe Ser Glu Leu Ala Thr | | |
| 220                 225                 230                 235 | | |
| aag tgc atc atc aag atc gtg gag ttt gcc aag cgg ttg cct ggc ttt | | 952 |
| Lys Cys Ile Ile Lys Ile Val Glu Phe Ala Lys Arg Leu Pro Gly Phe | | |
|                 240                 245                 250 | | |

-continued

```
aca ggg ctc agc att gct gac cag atc act ctg ctc aaa gct gcc tgc      1000
Thr Gly Leu Ser Ile Ala Asp Gln Ile Thr Leu Leu Lys Ala Ala Cys
        255                 260                 265 cta gat atc ctg atg ctg cgt atc tgc aca agg tac acc cca gag cag      1048
Leu Asp Ile Leu Met Leu Arg Ile Cys Thr Arg Tyr Thr Pro Glu Gln
            270                 275                 280 gac acc atg acc ttc tcc gac ggg ctg acc ctg aac cgg acc cag atg      1096
Asp Thr Met Thr Phe Ser Asp Gly Leu Thr Leu Asn Arg Thr Gln Met
285                 290                 295 cac aat gcc ggc ttc ggg ccc ctc aca gac ctt gtc ttt gcc ttt gct      1144
His Asn Ala Gly Phe Gly Pro Leu Thr Asp Leu Val Phe Ala Phe Ala
300                 305                 310                 315 ggg cag ctc ctg ccc ctg gag atg gat gac acc gag aca ggg ctg ctc      1192
Gly Gln Leu Leu Pro Leu Glu Met Asp Asp Thr Glu Thr Gly Leu Leu
                320                 325                 330 agc gcc atc tgc ctc atc tgc gga gac cgc atg gac ctg gag gag ccc      1240
Ser Ala Ile Cys Leu Ile Cys Gly Asp Arg Met Asp Leu Glu Glu Pro
            335                 340                 345 gaa aaa gtg gac aag ctg cag gag cca ctg ctg gaa gcc ctg agg ctg      1288
Glu Lys Val Asp Lys Leu Gln Glu Pro Leu Leu Glu Ala Leu Arg Leu
        350                 355                 360 tac gcc cgg cgc cgg cgg ccc agc cag ccc tac atg ttc cca agg atg      1336
Tyr Ala Arg Arg Arg Arg Pro Ser Gln Pro Tyr Met Phe Pro Arg Met
365                 370                 375 cta atg aaa atc acc gac ctc cgg ggc atc agc act aag gga gct gaa      1384
Leu Met Lys Ile Thr Asp Leu Arg Gly Ile Ser Thr Lys Gly Ala Glu
380                 385                 390                 395 agg gcc att act ctg aag atg gag att cca ggc ccg atg cct ccc tta      1432
Arg Ala Ile Thr Leu Lys Met Glu Ile Pro Gly Pro Met Pro Pro Leu
                400                 405                 410 atc cga gag atg ctg gag aac cct gaa atg ttt gag gat gac tcc tcg      1480
Ile Arg Glu Met Leu Glu Asn Pro Glu Met Phe Glu Asp Asp Ser Ser
            415                 420                 425 cag cct ggt ccc cac ccc aat gcc tct agc gag gat gag gtt cct ggg      1528
Gln Pro Gly Pro His Pro Asn Ala Ser Ser Glu Asp Glu Val Pro Gly
        430                 435                 440 ggc cag ggc aaa ggg ggc ctg aag tcc cca gcc tga cca ggc cga att c   1577
Gly Gln Gly Lys Gly Gly Leu Lys Ser Pro Ala     Pro Gly Arg Ile
445                 450                         455

<210> SEQ ID NO 2
<211> LENGTH: 454
<212> TYPE: PRT
<213> ORGANISM: Human
<220> FEATURE:
<221> NAME/KEY: misc_feature
<223> OTHER INFORMATION: Human Retinoic Acid Receptor-gamma (hRAR-gamma)

<400> SEQUENCE: 2

Met Ala Thr Asn Lys Glu Arg Leu Phe Ala Ala Gly Ala Leu Gly Pro
1               5                   10                  15

Gly Ser Gly Tyr Pro Gly Ala Gly Phe Pro Phe Ala Phe Pro Gly Ala
            20                  25                  30

Leu Arg Gly Ser Pro Pro Phe Glu Met Leu Ser Pro Ser Phe Arg Gly
        35                  40                  45

Leu Gly Gln Pro Asp Leu Pro Lys Glu Met Ala Ser Leu Ser Val Glu
    50                  55                  60

Thr Gln Ser Thr Ser Ser Glu Glu Met Val Pro Ser Ser Pro Ser Pro
65                  70                  75                  80

Pro Pro Pro Pro Arg Val Tyr Lys Pro Cys Phe Val Cys Asn Asp Lys
```

```
                      85                  90                  95
Ser Ser Gly Tyr His Tyr Gly Val Ser Ser Cys Glu Gly Cys Lys Gly
                100                 105                 110

Phe Phe Arg Arg Ser Ile Gln Lys Asn Met Val Tyr Thr Cys His Arg
                115                 120                 125

Asp Lys Asn Cys Ile Ile Asn Lys Val Thr Arg Asn Arg Cys Gln Tyr
            130                 135                 140

Cys Arg Leu Gln Lys Cys Phe Glu Val Gly Met Ser Lys Glu Ala Val
145                 150                 155                 160

Arg Asn Asp Arg Asn Lys Lys Lys Glu Val Lys Glu Glu Gly Ser
                165                 170                 175

Pro Asp Ser Tyr Glu Leu Ser Pro Gln Leu Glu Glu Leu Ile Thr Lys
            180                 185                 190

Val Ser Lys Ala His Gln Glu Thr Phe Pro Ser Leu Cys Gln Leu Gly
            195                 200                 205

Lys Tyr Thr Thr Asn Ser Ser Ala Asp His Arg Val Gln Leu Asp Leu
    210                 215                 220

Gly Leu Trp Asp Lys Phe Ser Glu Leu Ala Thr Lys Cys Ile Ile Lys
225                 230                 235                 240

Ile Val Glu Phe Ala Lys Arg Leu Pro Gly Phe Thr Gly Leu Ser Ile
                245                 250                 255

Ala Asp Gln Ile Thr Leu Leu Lys Ala Ala Cys Leu Asp Ile Leu Met
                260                 265                 270

Leu Arg Ile Cys Thr Arg Tyr Thr Pro Glu Gln Asp Thr Met Thr Phe
            275                 280                 285

Ser Asp Gly Leu Thr Leu Asn Arg Thr Gln Met His Asn Ala Gly Phe
290                 295                 300

Gly Pro Leu Thr Asp Leu Val Phe Ala Phe Ala Gly Gln Leu Leu Pro
305                 310                 315                 320

Leu Glu Met Asp Asp Thr Glu Thr Gly Leu Leu Ser Ala Ile Cys Leu
                325                 330                 335

Ile Cys Gly Asp Arg Met Asp Leu Glu Glu Pro Glu Lys Val Asp Lys
                340                 345                 350

Leu Gln Glu Pro Leu Leu Glu Ala Leu Arg Leu Tyr Ala Arg Arg Arg
            355                 360                 365

Arg Pro Ser Gln Pro Tyr Met Phe Pro Arg Met Leu Met Lys Ile Thr
            370                 375                 380

Asp Leu Arg Gly Ile Ser Thr Lys Gly Ala Glu Arg Ala Ile Thr Leu
385                 390                 395                 400

Lys Met Glu Ile Pro Gly Pro Met Pro Pro Leu Ile Arg Glu Met Leu
                405                 410                 415

Glu Asn Pro Glu Met Phe Glu Asp Asp Ser Ser Gln Pro Gly Pro His
            420                 425                 430

Pro Asn Ala Ser Ser Glu Asp Glu Val Pro Gly Gly Gln Gly Lys Gly
            435                 440                 445

Gly Leu Lys Ser Pro Ala
    450

<210> SEQ ID NO 3
<211> LENGTH: 462
<212> TYPE: PRT
<213> ORGANISM: Human
<220> FEATURE:
<221> NAME/KEY: misc_feature
<223> OTHER INFORMATION: Human Retinoic Acid Receptor-alpha (hRAR-alpha)
```

-continued

```
<400> SEQUENCE: 3

Met Ala Ser Asn Ser Ser Cys Pro Thr Pro Gly Gly His Leu
1               5                   10                  15

Asn Gly Tyr Pro Val Pro Tyr Ala Phe Phe Pro Met Leu
            20                  25                  30

Gly Gly Leu Ser Pro Pro Gly Ala Leu Thr Thr Leu Gln His Gln Leu
                35                  40                  45

Pro Val Ser Gly Tyr Ser Thr Pro Ser Pro Ala Thr Ile Glu Thr Gln
    50                  55                  60

Ser Ser Ser Ser Glu Glu Ile Val Pro Ser Pro Pro Ser Pro Pro Pro
65                  70                  75                  80

Leu Pro Arg Ile Tyr Lys Pro Cys Phe Val Cys Gln Asp Lys Ser Ser
                85                  90                  95

Gly Tyr His Tyr Gly Val Ser Ala Cys Glu Gly Cys Lys Gly Phe Phe
                100                 105                 110

Arg Arg Ser Ile Gln Lys Asn Met Val Tyr Thr Cys His Arg Asp Lys
            115                 120                 125

Asn Cys Ile Ile Asn Lys Val Thr Arg Asn Arg Cys Gln Tyr Cys Arg
130                 135                 140

Leu Gln Lys Cys Phe Glu Val Gly Met Ser Lys Glu Ser Val Arg Asn
145                 150                 155                 160

Asp Arg Asn Lys Lys Lys Glu Val Pro Lys Pro Glu Cys Ser Glu
                165                 170                 175

Ser Tyr Thr Leu Thr Pro Glu Val Gly Glu Leu Ile Glu Lys Val Arg
            180                 185                 190

Lys Ala His Gln Glu Thr Phe Pro Ala Leu Cys Gln Leu Gly Lys Tyr
                195                 200                 205

Thr Thr Asn Asn Ser Ser Glu Gln Arg Val Ser Leu Asp Ile Asp Leu
210                 215                 220

Trp Asp Lys Phe Ser Glu Leu Ser Thr Lys Cys Ile Ile Lys Thr Val
225                 230                 235                 240

Glu Phe Ala Lys Gln Leu Pro Gly Phe Thr Thr Leu Thr Ile Ala Asp
                245                 250                 255

Gln Ile Thr Leu Leu Lys Ala Ala Cys Leu Asp Ile Leu Ile Leu Arg
            260                 265                 270

Ile Cys Thr Arg Tyr Thr Pro Glu Gln Asp Thr Met Thr Phe Ser Asp
                275                 280                 285

Gly Leu Thr Leu Asn Arg Thr Gln Met His Asn Ala Gly Phe Gly Pro
290                 295                 300

Leu Thr Asp Leu Val Phe Ala Phe Ala Asn Gln Leu Leu Pro Leu Glu
305                 310                 315                 320

Met Asp Asp Ala Glu Thr Gly Leu Leu Ser Ala Ile Cys Leu Ile Cys
                325                 330                 335

Gly Asp Arg Gln Asp Leu Glu Gln Pro Asp Arg Val Asp Met Leu Gln
            340                 345                 350

Glu Pro Leu Leu Glu Ala Leu Lys Val Tyr Val Arg Lys Arg Arg Pro
355                 360                 365

Ser Arg Pro His Met Phe Pro Lys Met Leu Met Lys Ile Thr Asp Leu
370                 375                 380

Arg Ser Ile Ser Ala Lys Gly Ala Glu Arg Val Ile Thr Leu Lys Met
385                 390                 395                 400

Glu Ile Pro Gly Ser Met Pro Pro Leu Ile Gln Glu Met Leu Glu Asn
                405                 410                 415
```

-continued

```
Ser Glu Gly Leu Asp Thr Leu Ser Gly Gln Pro Gly Gly Gly Arg
            420                 425                 430

Asp Gly Gly Gly Leu Ala Pro Pro Gly Ser Cys Ser Pro Ser Leu
            435                 440                 445

Ser Pro Ser Ser Asn Arg Ser Ser Pro Ala Thr His Ser Pro
450                 455                 460

<210> SEQ ID NO 4
<211> LENGTH: 448
<212> TYPE: PRT
<213> ORGANISM: Human
<220> FEATURE:
<221> NAME/KEY: misc_feature
<223> OTHER INFORMATION: Human Retinoic Acid Receptor-beta (hRAR-beta)

<400> SEQUENCE: 4

Met Phe Asp Cys Met Asp Val Leu Ser Val Ser Pro Gly Gln Ile Leu
1               5                   10                  15

Asp Phe Tyr Thr Ala Ser Pro Ser Ser Cys Met Leu Gln Glu Lys Ala
            20                  25                  30

Leu Lys Ala Cys Phe Ser Gly Leu Thr Gln Thr Glu Trp Gln His Arg
        35                  40                  45

His Thr Ala Gln Ser Ile Glu Thr Gln Ser Thr Ser Ser Glu Glu Leu
    50                  55                  60

Val Pro Ser Ser Pro Ser Pro Leu Pro Pro Pro Arg Val Tyr Lys Pro
65                  70                  75                  80

Cys Phe Val Cys Gln Asp Lys Ser Ser Gly Tyr His Tyr Gly Val Ser
                85                  90                  95

Ala Cys Glu Gly Cys Lys Gly Phe Phe Arg Arg Ser Ile Gln Lys Asn
            100                 105                 110

Met Ile Tyr Thr Cys His Arg Asp Lys Asn Cys Val Ile Asn Lys Val
        115                 120                 125

Thr Arg Asn Arg Cys Gln Tyr Cys Arg Leu Gln Lys Cys Phe Glu Val
    130                 135                 140

Gly Met Ser Lys Glu Ser Val Arg Asn Asp Arg Asn Lys Lys Lys
145                 150                 155                 160

Glu Thr Ser Lys Gln Glu Cys Thr Glu Ser Tyr Glu Met Thr Ala Glu
                165                 170                 175

Leu Asp Asp Leu Thr Glu Lys Ile Arg Lys Ala His Gln Glu Thr Phe
            180                 185                 190

Pro Ser Leu Cys Gln Leu Gly Lys Tyr Thr Thr Asn Ser Ser Ala Asp
        195                 200                 205

His Arg Val Arg Leu Asp Leu Gly Leu Trp Asp Lys Phe Ser Glu Leu
    210                 215                 220

Ala Thr Lys Cys Ile Ile Lys Ile Val Glu Phe Ala Lys Arg Leu Pro
225                 230                 235                 240

Gly Phe Thr Gly Leu Ser Ile Ala Asp Gln Ile Thr Leu Leu Lys Ala
                245                 250                 255

Ala Cys Leu Asp Ile Leu Ile Leu Arg Ile Cys Thr Arg Tyr Thr Pro
            260                 265                 270

Glu Gln Asp Thr Met Thr Phe Ser Asp Gly Leu Thr Leu Asn Arg Thr
        275                 280                 285

Gln Met His Asn Ala Gly Phe Gly Pro Leu Thr Asp Leu Val Phe Thr
    290                 295                 300

Phe Ala Asn Gln Leu Leu Pro Leu Glu Met Asp Asp Thr Glu Thr Gly
305                 310                 315                 320
```

```
Leu Leu Ser Ala Ile Cys Leu Ile Cys Gly Asp Arg Gln Asp Leu Glu
            325                 330                 335

Glu Pro Thr Lys Val Asp Lys Leu Gln Glu Pro Leu Leu Glu Ala Leu
        340                 345                 350

Lys Ile Tyr Ile Arg Lys Arg Arg Pro Ser Lys Pro His Met Phe Pro
            355                 360                 365

Lys Ile Leu Met Lys Ile Thr Asp Leu Arg Ser Ile Ser Ala Lys Gly
        370                 375                 380

Ala Glu Arg Val Ile Thr Leu Lys Met Glu Ile Pro Gly Ser Met Pro
385                 390                 395                 400

Pro Leu Ile Gln Glu Met Met Glu Asn Ser Glu Gly His Glu Pro Leu
            405                 410                 415

Thr Pro Ser Ser Ser Gly Asn Thr Ala Glu His Ser Pro Ser Ile Ser
        420                 425                 430

Pro Ser Ser Val Glu Asn Ser Gly Val Ser Gln Ser Pro Leu Val Gln
        435                 440                 445
```

<210> SEQ ID NO 5
<211> LENGTH: 21
<212> TYPE: PRT
<213> ORGANISM: Artificial Sequence
<220> FEATURE:
<221> NAME/KEY: misc_feature
<223> OTHER INFORMATION: DNA binding domain motif of the steroid hormone
      superfamily
<221> NAME/KEY: misc_feature
<222> LOCATION: (2)..(20)
<223> OTHER INFORMATION: Xaa is any amino acid

<400> SEQUENCE: 5

```
Cys Xaa Xaa Cys Xaa Xaa Xaa Xaa Xaa Xaa Xaa Xaa Xaa Xaa Xaa
1               5                   10                  15

Xaa Cys Xaa Xaa Cys
            20
```

<210> SEQ ID NO 6
<211> LENGTH: 22
<212> TYPE: PRT
<213> ORGANISM: Artificial Sequence
<220> FEATURE:
<221> NAME/KEY: misc_feature
<223> OTHER INFORMATION: DNA binding domain motif of the steroid hormone
      superfamily
<221> NAME/KEY: misc_feature
<222> LOCATION: (2)..(21)
<223> OTHER INFORMATION: Xaa is any amino acid

<400> SEQUENCE: 6

```
Cys Xaa Xaa Cys Xaa Xaa Xaa Xaa Xaa Xaa Xaa Xaa Xaa Xaa Xaa Xaa
1               5                   10                  15

Xaa Xaa Cys Xaa Xaa Cys
            20
```

<210> SEQ ID NO 7
<211> LENGTH: 23
<212> TYPE: PRT
<213> ORGANISM: Artificial Sequence
<220> FEATURE:
<221> NAME/KEY: misc_feature
<223> OTHER INFORMATION: DNA binding domain motif of the steroid hormone
      superfamily
<221> NAME/KEY: misc_feature
<222> LOCATION: (2)..(22)
<223> OTHER INFORMATION: Xaa is any amino acid

<400> SEQUENCE: 7

```
Cys Xaa Xaa Cys Xaa Xaa Xaa Xaa Xaa Xaa Xaa Xaa Xaa Xaa Xaa
1               5                   10                  15

Xaa Xaa Xaa Cys Xaa Xaa Cys
            20
```